United States Patent [19]

Rittenhouse

[11] Patent Number: 4,770,994
[45] Date of Patent: Sep. 13, 1988

[54] DETERMINATION OF CARBOHYDRATE ACCEPTORS

[75] Inventor: Harry G. Rittenhouse, Lake Bluff, Ill.

[73] Assignee: Abbott Laboratories, Abbott Park, Ill.

[21] Appl. No.: 86,196

[22] Filed: Aug. 14, 1987

Related U.S. Application Data

[63] Continuation of Ser. No. 403,690, Jul. 30, 1982, abandoned.

[51] Int. Cl.$^4$ ............................ C12Q 1/5; C12Q 1/48; G01N 33/574
[52] U.S. Cl. .......................................... 435/7; 435/14; 435/15
[58] Field of Search ............................ 435/4, 7, 14, 15

[56] References Cited

U.S. PATENT DOCUMENTS 4,132,600 1/1979 Plotkin et al. ...................... 435/15
4,261,976 4/1981 Isselbacher et al. ................ 424/101

FOREIGN PATENT DOCUMENTS 0021310 7/1981 European Pat. Off. ............ 435/14

Primary Examiner—Esther M. Kepplinger
Attorney, Agent, or Firm—Martin L. Katz; Donna Bobrowicz

[57] ABSTRACT

A method for determining carbohydrate acceptors in a sample is disclosed wherein a sugar moiety is enzymatically transferred to the carbohydrate acceptor and the resulting carbohydrate acceptor-sugar complex is determined as a measure of the carbohydrate acceptor in the sample.

4 Claims, No Drawings

DETERMINATION OF CARBOHYDRATE ACCEPTORS

This application is a continuation, of application Ser. No. 403,690, filed July 30, 1982, now abandoned.

INTRODUCTION

The present invention relates to a method for determining carbohydrate acceptors in a biological sample. In particular, the present invention relates to a method for determining specific carbohydrate acceptors, the determination of which is useful in the diagnosis and/or treatment of cancer or other chronic disease.

BACKGROUND OF THE INVENTION

It has been reported that many patients, diagnosed as having cancer have elevated serum glycoprotein levels. Such increased glycoprotein levels may be due to increased shedding and/or secretion of glycoproteins by malignant cells or increased host synthesis of glycoproteins in response to a tumor. Efforts to accurately measure such tumor-related increases in total serum glycoprotein levels have been relatively unsuccessful, due in part to the fact that the actual increases in serum glycoprotein levels are small, serum glycoprotein levels vary from individual to individual, and with time, in the same individual.

Carbohydrate acceptors may be derived from tumors, i.e., tumor glycoproteins resulting from necrosis of the cell, or from a host in response to tissue destruction, i.e., produced as a result of tumor growth. Tumor growth provokes the migration of host macrophage and neutrophil cells to the vicinity of the tumor. When the host cells are brought in contact with the tumor cells, degradative enzymes present in host cell lysosomes are released. Lysosomes contain a variety of glycosidases including, for example, sialidase and $\beta$-galactosidase, which are capable of producing glycoproteins having terminal N-acetylglucosamine moieties. Other lysosomal glycosidases, such as, N-acetylglucosaminidase, sequentially degrade the entire oligosaccharide group of glycoproteins, thereby creating other terminal carbohydrates. Each of these terminal carbohydrates have the potential to serve as acceptors for the appropriate sugar derivatives and glycosyltransferases. Increased steady state levels of these partially-degraded glycoproteins may be expected in samples obtained from patients having cancer or other chronic diseases due to continuous production of such glycoproteins in the serum of such patients. The increase in the level of partially-degraded glycoproteins may also be due to the inefficient removal of various types of degraded glycoproteins. For example, the turnover or removal of glycoproteins with newly-exposed mannose residues may be slower than the corresponding galactose-terminal glycoproteins, An additional source of glycoproteins with incomplete oligosaccharides may be due to aborted glycosylation of tumor cell glycoproteins. Increased levels of incomplete glycoproteins in serum may result from the destruction of tumor cells by host response and/or by an ineffective system of glycosyltransferases within the tumor cell due to oncogenic transformation. In addition, the host may respond to the presence of a tumor by producing blood glycoproteins which contain sugar acceptor sites.

Although several specific glycoproteins, characteristically found in cancer patients, have been identified, there is no rapid method or procedure for quantitatively determining carbohydrate acceptor subclasses having common oligosaccharide moieties. Davidson, et al, in U.S. Pat. No. 4,146,603 describes a tumor specific glycoprotein characterized as having an isoelectric point of from 4.2 to 4.6 and solubility in perchloric acid. The described tumor specific glycoproteins are detected by mixing a serum sample with perchloric acid to precipitate a fraction and then subjecting the perchloric acid soluble fraction to gel electrophoresis or isoelectric focusing to detect the presence of a tumor specific glycoprotein. Isselbacher, et al, in U.S. Pat. No. 4,261,976 discloses a glycopeptide which inhibits the growth of malignant cells or malignant tumors. The glycopeptide, obtained from animals or humans having malignant cells or tumors, is soluble in phosphotungstic acid and has a molecular weight of about 3600 and is a substrate for isoenzymes of serum galactosyltransferase (GT-I and GT-II). The presence of the glycopeptide is indicated by measuring a known amount of galactosyltransferase in the sample containing the glycopeptide. Plotkin, et al. in U.S. Pat. No. 4,132,600 describes an enzymatic noninvasive method for detecting cancer in mammalian tissue comprising incubation of urine containing exfoliated cells from mammalian tissues suspected of containing cancerous cells and then measuring the galactosyltransferase activity of the cells. Plotkin, et al, in W.O. No. 80/02296 describes a method for determining whether mammalian tissue cells are malignant by assaying cells from said tissues to determine whether the glycoproteins are significantly altered compared to nonmalignant cells. The glycoproteins are indirectly measured by adding to the cells a marker, i.e., a lectin, capable of being detected by nonchemical technique, wherein said marker has a specific affinity for galactose or galactose residue, and thereafter detecting the amount of marker bound to said cells.

It is an object of the present invention to provide a method for directly detecting and quantitatively measuring in a biological sample the level of carbohydrate acceptors, in particular, subclasses of glycoproteins having common oligosaccharide moieties.

SUMMARY OF THE INVENTION

The present invention relates to a method for determining a carbohydrate acceptor in a sample comprising:

(a) producing a carbohydrate acceptor-sugar complex by intermixing with the sample containing the carbohydrate acceptor of interest (i) a donor comprising a sugar-nucleotide conjugate wherein the sugar moiety of the donor is capable of specifically binding to the carbohydrate acceptor of interest;

(ii) an enzyme source capable of catalyzing the reaction of the carbohydrate acceptor and the donor; wherein effective amounts of donor and enzyme source are added so as to produce an amount of carbohydrate acceptor-sugar complex related to the amount of carbohydrate acceptor present in the sample; then (b) determining the amount of carbohydrate acceptor-sugar complex produced as a measure of the amount of carbohydrate acceptor present in the sample.

The method of the present invention is of particular interest in determining carbohydrate acceptors and in particular glycoproteins that are useful in the diagnosis and treatment of various types of cancer and other chronic diseases.

The present invention further relates to a galactose acceptor protein (GAP) characterized as an acceptor protein capable of reacting with uridine 5'-diphosphate-galactose (UDP-galactose) and adenosine 5'-triphosphate in the presence of manganous chloride to form a complex that is insoluble in perchloric acid and phosphotungstic acid and has a subunit molecular weight of approximately 60,000–80,000 daltons as determined by polyacrylamide gel electrophoresis using sodium dodecyl sulfate. The determination of this galactose acceptor protein is useful in the diagnosis and/or treatment of cancer or other chronic disease.

DETAILED DESCRIPTION OF THE INVENTION

The term "carbohydrate acceptor" refers to a class of molecules having recognition sites for glycosyltransferases and capable of accepting a sugar moiety of a sugar-nucleotide conjugate, wherein the acceptance of the sugar moiety is catalyzed by a glycosyltransferase specific to the carbohydrate acceptor of interest and the sugar-nucleotide conjugate. The carbohydrate acceptors determined by the methods of the present invention include glycoproteins, glycolipids, glycopeptides and polysaccharides. Of particular interest are glycoproteins containing terminal carbohydrate moieties reflecting incomplete glycosylation. Included within the scope of the term "carbohydrate acceptor" are terminal carbohydrate moieties present in oligosaccharide sequences of N-linked and O-linked glycoproteins. The incomplete oligosaccharide chains permit specific enzymatic or chemical labeling of the altered glycoproteins.

In accordance with one specific embodiment of the method of the present invention, a mixture containing a serum sample, labeled donor, and enzyme source are incubated for a period of time sufficient to produce a detectable carbohydrate acceptor-sugar complex. The enzyme catalyzed reaction is terminated and the amount of complex produced is determined as a measure of the carbohydrate acceptor in the sample. The reaction time required to produce a detectable carbohydrate acceptor-sugar complex is not critical. The reaction time will vary depending on factors, such as, for example, concentrations of carbohydrate acceptors in the sample, concentration of the reagents, and the like; and is readily ascertained by one of ordinary skill in the art. The method of the present invention is illustrated by the following reaction scheme:

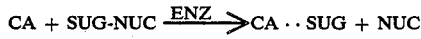

$$CA + SUG\text{-}NUC \xrightarrow{ENZ} CA \cdots SUG + NUC$$

wherein CA is a carbohydrate acceptor; SUG-NUC is a donor comprising a sugar-nucleotide conjugate; ENZ is an enzyme specific to the carbohydrate acceptor and donor; CA ... SUG is a carbohydrate acceptor-sugar complex produced; and NUC is a nucleotide released.

The donor substrates employed in the method of the present invention comprise sugar-nucleotide conjugates capable of being specifically recognized by the carbohydrate acceptor to be determined. That is, the carbohydrate acceptor is capable of accepting the sugar portion of the sugar-nucleotide conjugate in the presence of an enzyme and if necessary, a substrate diverter. For example, in a determination of serum glycoproteins having terminal N-acetylglucosamine residues, uridine 5'-diphosphate-galactose (UDP-galactose) is employed as a donor to produce a N-acetylglusosamine-galactose complex. Donors may be labeled with various "tags" thereby resulting in the formation of readily detectable carbohydrate acceptor-sugar complexes. Such "tags" are well known in the art and include enzyme-tags, fluorescent-tags or radioisotope-tags. It is preferred to employ donors that are radiolabeled. Such radiolabeled donors may be tagged with radiolabels such as, for example, tritium ($^3H$), carbon-14 ($^{14}C$) and the like. It is preferred that tritium ($^3H$) be utilized as the radioactive tag when a radiolabeled donor is employed in the methods of the present invention. The particular donor employed, whether labeled or unlabeled, is readily ascertained by one of ordinary skill in the art depending on the carbohydrate acceptor to be determined. Donors, labeled or unlabeled, useful in the present invention are either commercially available or readily synthesized using conventional techniques. The amount of donor employed varies depending on the specific activity of the system, i.e., the particular carbohydrate acceptor to be determined and the particular enzyme employed; and is readily ascertained by one of ordinary skill in the art.

As previously noted, the method of the present invention requires the enzymatic transfer of a sugar moiety to a carbohydrate acceptor. The enzyme source employed in the method of the present invention specifically catalyzes the reaction of the carbohydrate acceptor and the donor. The particular enzyme source employed is determined by the carbohydrate acceptor to be assayed and the particular donor employed. Enzyme sources, including enzymes, isoenzymes, and variants, are known in the art and the particular enzyme source required is readily ascertained by one of ordinary skill in the art depending on the specific carbohydrate acceptor donor system utilized. For example, in an assay for serum glycoproteins containing terminal N-acetylglucosamine residues utilizing UDP-galactose as a donor, galactosyltransferase is employed as the enzyme. In addition, certain enzymes require the presence of a cofactor in order to increase enzyme activity. Such cofactors are well known in the art and the specific cofactor to be employed is readily ascertained by one of ordinary skill in the art. For example, if galactosyltransferase is employed as the enzyme source, manganous chloride is utilized as a cofactor. The concentration of the enzyme source employed varies depending upon the specific activity of the system, i.e., the particular carbohydrate acceptor to be determined, the specific donor and enzyme source employed; and is readily ascertained by one of ordinary skill in the art. However, it should be noted that although the serum sample to be assayed may contain a certain amount of an enzyme, the method of the present invention preferable requires the addition of an exogenous enzyme source, generally in quantities well in excess of the amount of enzymes normally found in serum. In other words, the carbohydrate acceptor is the limiting reagent. Thus, the enzyme and donor concentrations are adjusted so that the amount of carbohydrate acceptor-sugar conjugate formed will be related to the concentration of the carbohydrate acceptor present and not limited to either donor or enzyme concentration.

In addition, to a donor and enzyme source, the method of the present invention may require the presence of a substrate diverter in order to produce a detectable carbohydrate sugar complex. Depending on the specific donor or concentration of the donor, employed in the system, a substrate diverter may be required to prevent degradation of the donor, thereby permitting the sugar moiety of the sugar-nucleotide conjugate to specifically bind to the carbohydrate acceptor to be determined. A substrate diverter may be required when the donor concentration is low or wherein the specific donor utilized has bonds susceptible to cleavage by serum enzymes. Substrate diverters are well known in the art and the particular substrate diverter required is readily ascertained by one of ordinary skill in the art depending on the specific donor utilized and carbohydrate acceptor to be determined, For example, in accordance with the present invention an assay for serum glycoproteins containing a terminal N-acetylglucosamine residue, utilizes adenosine 5'-triphosphate (ATP) as a substrate diverter in order to prevent the degradation of the UDP-galactose donor by serum nucleotide pyrophosphatase.

The temperature at which the methods of the present invention are employed is generally the optimal temperature for enzymatic activity of the particular system. The temperature will generally vary depending upon the specific enzyme source. In addition, it is preferred that the temperature be held essentially constant, preferably, ±5° C. of the optimal temperature and most preferably ±2° C. of the optimal temperature.

The amount of carbohydrate acceptor-sugar complex found as a result of the enzyme catalyzed reaction, is determined as a measure of the carbohydrate acceptor present in the sample. The amount of particular carbohydrate acceptor determined in a sample obtained from a patient having or suspected of having cancer or other malignant disease is compared with the amount of the carbohydrate acceptor found in a normal sample obtained from a healthy patient as a means of determining the amount of carbohydrate acceptor associated with the particular disease.

The carbohydrate acceptor-sugar complex formed may be directly determined if a labeled donor is employed. If a labeled donor, for example a donor containing a radiolabeled sugar moiety is utilized, a radiolabeled carbohydrate acceptor-sugar complex is formed and is measured using conventional radiochemical techniques. In addition, if a labeled donor is employed, the enzyme catalyzed reaction of the carbohydrate acceptor and donor is terminated prior to determining the amount of carbohydrate acceptor-sugar complex produced. Methods for terminating such reactions are well known in the art and include for example inactivation of the enzyme source by adding a large excess of unlabeled donor, heat treatment, i.e., increasing the temperature to inactivate the enzyme, if a cofactor is employed, binding of the cofactor and the like. If a radiolabeled donor is employed, it is preferred to terminate the enzyme catalyzed reaction by adding a large excess of unlabeled donor. It is also necessary to separate the labeled carbohydrate acceptor-sugar complex formed from unreacted labeled donor prior to determining the amount of labeled carbohydrate acceptor-sugar complex produced. For example, if the carbohydrate acceptor to be determined is a glycoprotein, the carbohydrate acceptor-sugar complex may be separated by precipitating the complex in phosphotungstic acid. Similarly, if a glycolipid is to be determined, the corresponding carbohydrate acceptor-sugar complex produced may be separated using lipid extraction techniques.

If an unlabeled donor is utilized, the amount of carbohydrate acceptor-sugar complex produced may be indirectly measured by determining the amount of nucleotide released upon reaction of the carbohydrate acceptor and donor. For example, if UDP-galactose is employed as the donor, UDP is released upon reaction with the carbohydrate acceptor in the sample. The amount of UDP thus produced is determined by enzymatically converting the released UDP nucleotide to a product which can subsequently produce reduced nicotinamide adenine dinucleotide (NADH). The NADH thus produced is a measure of the carbohydrate acceptor sugar complex formed.

It should be noted that the concentrations of the donor and enzyme source (endogenous and/or exogenous) are not narrowly critical. Effective amounts of donor and enzyme source are added so that sufficient sugar is transferred from the donor to the carbohydrate acceptor to produce an amount of carbohydrate acceptor-sugar complex related to the amount of carbohydrate acceptor in the sample. Effective amounts of donor and enzyme source are readily ascertained by one of ordinary skill in the art. Effective amounts of donor are at least equal to and preferably in excess of the amount of carbohydrate acceptor in the same. Effective amounts of enzyme are at least equal to and preferably greater than the amount of enzyme necessary to completely catalyze the transfer of sugar from the donor to the carbohydrate acceptor.

It should be noted that the samples to be assayed do not require any special handling precautions generally associated with enzymatic procedures due to the fact that excess enzyme is added during the assay itself. Therefore, degradation of endogenous enzyme by elevated temperatures, such as due to incubation of the sample, time, freeze-thaw, etc., is of no consequence and will not affect assay results.

In addition the type of samples to be assayed for carbohydrate acceptors include biological specimens, such as, for example, body fluids, tissue specimens, and serum. For increased sensitivity and specificity, as well as ease of operation, serum samples are preferred.

Table I serves to illustrate various donors, enzymes, and substrate diverters that may be utilized in the determination of specific carbohydrate acceptors in accordance with the methods of the present invention. The following abbreviations are employed in Table I:
UDP—uridine 5'-diphosphate;
CMP—cytidine monophosphate;
GDP—guanosine diphosphate;
ATP—adenosine 5'-triphosphate;
AMP—adenosine monophosphate;
CTP—cytidine triphosphate.

TABLE I

CARBOHYDRATE ACCEPTOR ASSAY SYSTEMS

| Carbohydrate Acceptor | Donor* | Enzyme | Substrate Diverter |
|---|---|---|---|
| Galactose Acceptor Protein | UDP-Galactose | Galactosyltransferase | ATP |
| Sialic Acid Acceptor Protein | CMP-Sialic Acid | Sialyltransferase | AMP |
| Fucosyl Acceptor Protein | GDP-Fucose | Fucosyltransferase | CTP |
| N—Acetylgalactosamine Acceptor Protein | UDP-N—Acetylgalactosamine | N—Acetylgalactosaminyltransferase | ATP |
| N—Acetylglucosamine | UDP-N—Acetylglucosamine | N—Acetylglucosaminyltransferase | ATP |

TABLE I-continued

CARBOHYDRATE ACCEPTOR ASSAY SYSTEMS

| Carbohydrate Acceptor | Donor* | Enzyme | Substrate Diverter |
|---|---|---|---|
| Acceptor Protein | | | |

*If a labeled donor is employed, a tritium ($H^3$) tag may be utilized, i.e., UDP-($^3$H)—galactose, etc.

Table I represents various assay systems that may be employed in accordance with the methods of the present invention. As one of ordinary skill in the art will readily ascertain, numerous other systems may be readily developed. As is well known in the art, each carbohydrate acceptor contains specific glycosidic linkages to which the sugar moiety may be transferred. To further increase resolution and specificity, one may employ a specific subclass of each enzyme which catalyzes the transfer of a sugar moiety to a carbohydrate acceptor resulting in a particular molecular linkage. For example, in an assay for serum glycoproteins containing terminal N-acetylglucosamine residues, employing UDP-galactose as a donor, will utilize a specific transferase subclass of galactosyltransferase to transfer galactose to a $\beta 1 \rightarrow 4$ linkage and a different transferase subclass of galactosyltransferase to transfer galactose to a $\beta 1 \rightarrow 3$ linkage. The specific subclass of each enzyme that may be required is readily ascertained by one of ordinary skill in the art and depends on the molecular linkage desired. The present invention may be further and more specifically described by reference to the following examples.

EXAMPLE I

To 30 μl of a serum sample on a microtiter plate is added 60 μl of a solution containing 0.62 μCi of ($^3$H) UDP-Galactose, 10.0 μl of 10mM ATP (pH 6.8), 10.0 μl of 0.1M MnCl$_2$, 30.0 μl of 0.1M sodium cacodylate (pH 7.4), 10.0 μl of bovine milk galactosyltransferase (100 μl Prot/ml, 0.45 units/ml; wherein one unit catalyzes the transfer of 1μ mole galactose/minute at 30° C.) and 4.0 μl of 1000p Mol/μl of unlabeled UDP-galactose. The microtiter plate is sealed with precut acetate plate sealers. The reaction mixture is incubated at 37° C. in a waterbath for sixty minutes. Following the incubation period, the acetate plate cover is removed and the microtiter plate is placed on wet ice. To the reaction mixture is added 10 μl of unlabeled UDP-galactose (10 mM). The resulting mixture containing a radiolabeled GAP-galactose complex is applied to a glass fiber sheet Whatman No. 934-AH glass microfibre filters). The glass fiber sheet is dried in an oven at 80° C. for 8–10 minutes. The dried glass fiber sheet is placed on a filter paper previously wetted with 5% phosphotungstic acid in 0.2N HCl. After five minutes, the glass fiber sheet is placed in a solution containing 5% phosphotungstic acid in 0.2N hydrochloric acid. After fifteen minutes, the glass fiber sheet is removed from the phosphotungstic acid solution, blotted between paper towels, and transferred to a 0.1N hydrochloric acid solution. After ten minutes, the glass fiber sheet is removed from the hydrochloric acid solution, blotted with paper towels and transferred to a second 0.1N hydrochloric acid solution. After an additional ten minute period, the glass fiber sheet is removed from the hydrochloric acid solution, blotted between paper towels and transferred to a solution containing absolute ethanol. After five minutes, the glass fiber sheet is removed from the ethanol, blotted between paper towels and transferred to a second ethanol solution. After an additional five minute period, the glass fiber sheet is removed from the ethanol solution, blotted between paper towels and dried in an oven at 80° C. for ten minutes. The glass fiber sheet containing the radiolabeled GAP-galactose complex is placed in a scintillation vial and 10 ml of a scintillation solution (INSTA-GEL) are added and the labeled conjugate ($^3$H) precipatated on the glass fiber sheet is counted for 1-2 minutes using a TRI-CARB liquid scintillation counter.

EXAMPLE II

The galactose acceptor protein-galactose complex formed (GAP-galactose) has been characterized as having the following properties:

(1) the major serum radiolabeled GAP-galactose complex has a subunit molecular weight of approximately 60,000–80,000 as determined using polyacrylamide gel electrophoresis (10–20% gradient) in the presence of 0.1% sodium dodecyl sulfate, followed by autofluorography;

(2) greater than 50% of the total GAP-galactose complex are precipitated using 50% saturated ammonium sulfate;

(3) the GAP-galactose complex is insoluble in 5% phosphotungstic acid; and (4) greater than 90% of the GAP-galactose complex is insoluble in 0.6M perchloric acid at 0° C.

As previously noted, the method described herein is useful in assaying for carbohydrate acceptors and provides a procedure useful in the diagnosis and/or treatment of cancer and other malignant diseases. Employing the procedures described in Example I, the galactose acceptor protein characterized in Example II, has been found to be in increased levels in 154 out of 239 (64.4%) of serum samples obtained from patients previously diagnosed as having various types of cancer such as for example, colon, breast, lung and pancreatic cancer; as well as other malignant diseases such as Hodgkins disease. In addition, the determination of carbohydrate acceptors, in particular the galactose acceptor protein characterized in Example II, in accordance with the method of the present invention, is useful in combination with other assays for cancer-markers, such as an assay for carcinoembryonic antigen (CEA), for the diagnosis and treatment of cancer and other malignant disease.

Those skilled in the art will recognize, or be able to ascertain using no more than routine experimentation, many equivalents to the specific embodiments to the invention described herein. Such equivalents are intended to be within the spirit and scope of the following claims.

What is claimed is:

1. A method for determining elevated levels of incompletely glycosylated glycoprotein tumor markers in samples from cancer patients comprising;
   (a) intermixing with said sample containing said glycoprotein;
      (i) a sugar-nucleotide conjugate donor wherein the sugar moiety of said donor is capable of covalently labeling said glycoprotein; and (ii) an excess of exogenous enzyme capable of catalyzing the reaction of said glycoprotein and said donor; and
(iii) a substrate diverter capable of preventing degradation of said donor, thereby enabling said sugar moiety to bind to said glycoprotein;
(b) terminating the reaction of said glycoprotein and donor; then
(c) determining the amount of incompletely glycosylated glycoprotein-sugar complex produced as a measure of the amount of said glycoprotein present in the sample.

2. A method according to claim 1 wherein a radiolabeled sugar-nucleotide conjugate is employed as the donor.

3. A method according to claim 4 wherein the sample is a serum sample.

4. A method according to claim 1 wherein a cofactor is added to the enzyme.

* * * * *